United States Patent [19]
Clement

[11] Patent Number: 5,527,332
[45] Date of Patent: Jun. 18, 1996

[54] TISSUE CUTTER FOR SURGERY

[75] Inventor: Thomas P. Clement, Bloomfield, Ind.

[73] Assignee: Mectra Labs, Inc., Bloomfield, Ind.

[21] Appl. No.: 333,424

[22] Filed: Nov. 2, 1994

[51] Int. Cl.$^6$ .................................................. A61B 17/32
[52] U.S. Cl. ............................................. 606/171; 604/35
[58] Field of Search ................................ 604/35, 19, 21, 604/46; 606/2–3, 32, 15–18, 106–107, 110, 113–115, 159, 167, 170–171, 181–183

[56] References Cited

U.S. PATENT DOCUMENTS

| 628,907 | 7/1899 | Hart . |
| 786,215 | 3/1905 | Hepnar . |

(List continued on next page.)

FOREIGN PATENT DOCUMENTS

| 0350291 | 1/1990 | European Pat. Off. . |
| 2332743 | 6/1977 | France . |
| 3528656 | 7/1986 | Germany . |
| 4120329 | 1/1992 | Germany . |
| 991478 | 5/1965 | United Kingdom . |
| 81/031225 | 11/1981 | WIPO . |

OTHER PUBLICATIONS

K. Semm, "Pelviscopy–Oberative Guidelines," Kiel, Germany, 1988, pp. 53–54.
Pentax Precision Instrument Corp., "Gastrofiberscope," Surgical Products, Mar. 1990, vol. 9, No. 6, p. 13.
Storz, "Laparoscopic Cholecystectomy for the General Surgeon–Its Time Has Come," Surgical Products, May 1990, vol. 9, No. 6, p. 13.
Pentax Precision Instrument Corp., "GI Fiberscopes," Surgical Products, May 1990, vol. 9, No. 6, p. 13.
Healthco International Handbook, 1990, p. 116.
Storz, "The World of Endoscopy, " Semm Instruments for Operative Pelviscopy, 4th Edition, Mar. 1987, pp. 1–4.
Richard Wolf, cat. pg. and sketch/admitted prior art.
American Surgical Instruments, Inc., "Nexhat–Dorsey Disposable Hydro–Dissection Trumpet Valve," 3 Sheets, Mar. 19, 1990.
Richard Wolf, "The Complete Endoscopy Manufacturer," Surgical Products, May 1990, vol. 9, No. 6, p. 20.
Johnson & Johnson Medical Inc., "CIDEX is safe for scopes. Don't take our word for it." Surgical Products, May 1990, vol. 9, No. 6, p. 25.
Pentax®, "Pentax® PNE11 Bronchofiberscopes," Surgical Products, May 1990, vol. 9, No. 6, p. 44.
Pentax Precision Instrument Corp., "Therapeutic Gastrofiberscope with Water Jet," Sep. 1990, vol. 10, No. 1, p. 39.
Cabot Medical, "Suction/Irrigation Probe," Surgical Products, Nov. 1990, vol. 10, No. 11, p. 29.
EndoDynamics, Inc., "Aspiration Device," Surgical Products, Nov. 1990, vol. 10, No. 11, p. 30.
"Irrigation/Aspiration Probe," Surgical Products, Sep. 1990, vol. 10, No. 1, p. 28.

(List continued on next page.)

Primary Examiner—Stephen C. Pellegrino
Assistant Examiner—Nancy Mulcare
Attorney, Agent, or Firm—Barnes & Thornburg

[57] ABSTRACT

A surgical cutter is provided for removing body tissue during surgery. The surgical cutter includes a cannula having a proximal end and a distal end and a side wall defining an interior region. The distal end of the cannula is positioned inside a patient's body during surgery with the proximal end situated outside of the patient's body. The side wall of the cannula is formed to include an orifice for receiving body tissue. The surgical cutter further includes a first annular wall fixed to the distal end of the cannula and an annular intermediate wall. The first annular wall is arranged to define an annular gap disposed between the first annular wall and the cannula side wall. The annular intermediate wall includes an annular distal edge sized to be received by the gap. The annular intermediate wall and the cannula are arranged for relative axial movement between a first position with the intermediate wall remote from the orifice and a second position with the intermediate wall received in the gap to cut tissue received in the orifice.

50 Claims, 2 Drawing Sheets

U.S. PATENT DOCUMENTS

| | | |
|---|---|---|
| 811,111 | 1/1906 | Wegefarth . |
| 1,585,934 | 5/1926 | Muir . |
| 1,658,754 | 2/1928 | Wood . |
| 2,437,329 | 3/1948 | Moore . |
| 2,708,437 | 5/1955 | Hutchins . |
| 2,715,899 | 8/1955 | MacLean . |
| 2,812,765 | 11/1957 | Tofflemire . |
| 3,012,752 | 12/1961 | Buck . |
| 3,048,192 | 8/1962 | Murphy, Jr. . |
| 3,081,770 | 3/1963 | Hunter . |
| 3,109,426 | 11/1963 | Noonan et al. . |
| 3,157,201 | 11/1964 | Littmann . |
| 3,173,414 | 3/1965 | Guillant . |
| 3,434,691 | 3/1969 | Hamilton . |
| 3,467,082 | 9/1969 | Gilbert . |
| 3,682,177 | 8/1972 | Ames et al. . |
| 3,735,751 | 5/1973 | Katz . |
| 3,783,900 | 1/1974 | Waldbillig . |
| 3,788,602 | 1/1974 | Kitzie . |
| 3,794,032 | 2/1974 | Derouineau . |
| 3,833,000 | 9/1974 | Bridgman . |
| 3,834,372 | 9/1974 | Turney . |
| 3,837,345 | 9/1974 | Matar . |
| 3,853,127 | 12/1974 | Spademan . |
| 3,902,498 | 9/1975 | Niederer . |
| 3,957,082 | 5/1976 | Fuson et al. . |
| 3,994,287 | 11/1976 | Turp . |
| 3,995,619 | 12/1976 | Glatzer . |
| 4,011,869 | 3/1977 | Seiler, Jr. . |
| 4,016,881 | 4/1977 | Rioux et al. . |
| 4,037,599 | 7/1977 | Raulerson . |
| 4,043,322 | 8/1977 | Robinson . |
| 4,073,297 | 2/1978 | Kopp . |
| 4,079,737 | 3/1978 | Miller . |
| 4,099,529 | 7/1978 | Peyman . |
| 4,111,207 | 9/1978 | Seiler, Jr. . |
| 4,173,328 | 11/1979 | Karbo . |
| 4,177,814 | 12/1979 | Knepshield et al. . |
| 4,198,959 | 4/1980 | Otani . |
| 4,210,146 | 7/1980 | Banko . |
| 4,230,128 | 10/1980 | Aramayo . |
| 4,240,411 | 12/1980 | Hosono . |
| 4,261,357 | 4/1981 | Kontos . |
| 4,280,498 | 7/1981 | Jensen . |
| 4,282,873 | 8/1981 | Roth . |
| 4,282,884 | 8/1981 | Boebel . |
| 4,299,217 | 11/1981 | Sagae et al. . |
| 4,314,560 | 2/1982 | Helfgott et al. . |
| 4,314,586 | 2/1982 | Folkman . |
| 4,368,734 | 1/1983 | Banko . |
| 4,379,458 | 4/1983 | Bauer et al. . |
| 4,397,335 | 8/1983 | Doblar et al. . |
| 4,400,168 | 8/1983 | Buechel et al. . |
| 4,414,974 | 11/1983 | Dotson et al. . |
| 4,430,081 | 2/1984 | Timmermans . |
| 4,443,220 | 4/1984 | Hauer et al. . |
| 4,444,184 | 4/1984 | Oretorp . |
| 4,445,517 | 5/1984 | Feild . |
| 4,468,216 | 8/1984 | Muto . |
| 4,491,132 | 1/1985 | Aikins . |
| 4,512,344 | 4/1985 | Barber . |
| 4,519,385 | 5/1985 | Atkinson et al. . |
| 4,531,935 | 7/1985 | Berryessa . |
| 4,540,156 | 9/1985 | Cross . |
| 4,552,146 | 11/1985 | Jensen et al. . |
| 4,553,957 | 11/1985 | Williams et al. . |
| 4,553,964 | 11/1985 | Sasaki . |
| 4,566,480 | 1/1986 | Parham . |
| 4,568,332 | 2/1986 | Shippert . |
| 4,577,629 | 3/1986 | Martinez . |
| 4,581,014 | 4/1986 | Millerd et al. . |
| 4,589,414 | 5/1986 | Yoshida et al. . |
| 4,593,717 | 6/1986 | Levasseur . |
| 4,595,005 | 6/1986 | Jinotti . |
| 4,605,396 | 8/1986 | Tseo et al. . |
| 4,642,090 | 2/1987 | Utrata . |
| 4,642,097 | 2/1987 | Siposs . |
| 4,643,197 | 2/1987 | Greene et al. . |
| 4,644,951 | 2/1987 | Bays . |
| 4,645,496 | 2/1987 | Oscarsson . |
| 4,648,868 | 3/1987 | Hardwick et al. . |
| 4,651,753 | 3/1987 | Lifton . |
| 4,654,027 | 3/1987 | Dragan et al. . |
| 4,662,871 | 5/1987 | Rafelson . |
| 4,667,927 | 5/1987 | Oscarsson . |
| 4,674,500 | 6/1987 | DeSatnick . |
| 4,676,242 | 6/1987 | Doi . |
| 4,681,123 | 7/1987 | Valtchev . |
| 4,690,672 | 9/1987 | Veltrup . |
| 4,692,140 | 9/1987 | Olson . |
| 4,702,260 | 10/1987 | Wang . |
| 4,708,147 | 11/1987 | Haags . |
| 4,715,360 | 12/1987 | Akui et al. . |
| 4,735,606 | 4/1988 | Davison . |
| 4,758,235 | 7/1988 | Tu . |
| 4,793,359 | 12/1988 | Sharrow . |
| 4,807,666 | 2/1989 | Morse . |
| 4,808,155 | 2/1989 | Mahurkar . |
| 4,810,244 | 3/1989 | Allen . |
| 4,881,550 | 11/1989 | Kothe . |
| 4,900,300 | 2/1990 | Lee . |
| 4,911,202 | 3/1990 | Nelson . |
| 4,925,450 | 5/1990 | Imonti et al. . |
| 4,932,957 | 6/1990 | Zwick . |
| 4,958,621 | 9/1990 | Topel et al. . |
| 4,966,551 | 10/1990 | Betush . |
| 4,994,067 | 2/1991 | Summers . |
| 4,994,079 | 2/1991 | Genese et al. . |
| 5,019,035 | 5/1991 | Missirlian et al. . |
| 5,019,054 | 5/1991 | Clement et al. . |
| 5,053,044 | 10/1991 | Mueller et al. . |
| 5,078,688 | 1/1992 | Lobodzinski et al. . |
| 5,106,364 | 4/1992 | Hayafuji et al. . |
| 5,250,065 | 10/1993 | Clement et al. . |
| 5,273,524 | 12/1993 | Fox et al. . |
| 5,275,609 | 1/1994 | Pingleton et al. . |
| 5,282,790 | 2/1994 | Clement . |
| 5,306,237 | 4/1994 | Clement et al. . |
| 5,335,671 | 8/1994 | Clement . |
| 5,338,292 | 8/1994 | Clement et al. . |
| 5,374,244 | 12/1994 | Clement . |

OTHER PUBLICATIONS

Cabot Medical, "Larparoscopic Cholecystectomy From the Company Who Knows Laparoscopy," Surgical Products, Jan. 1991, vol. 10, No. 3, p. 4.

Olympus, "The Olympus Laparoscopic Cholecystectomy System: Resoultion for Gallstones, with the leader in High–Resolution Optics," Surgical Products, Jan. 1990, vol. 10, No. 3, p. 8.

Apple Medical, "Hunt/Reich Secondary Cannula," Surgical Products, May 1991, vol. 10, No. 7, p. 5.

Baxter Healthcare Corp., "Infusion Pump," Surgical Products, Jun. 1991, vol. 10, No. 8, p. 32.

Core Dynamics™ Inc., "Disposable Trocar with Reusable Cannula," Surgical Products, Jun. 1991, vol. 10, No. 8, p. 4.

TISSUE CUTTER FOR SURGERY

BACKGROUND AND SUMMARY OF THE INVENTION

The present invention relates to assemblies for performing surgery and particularly to tissue cutters for surgery having concentric cannulas with tip ends configured to allow cutting. Such cutters are particularly applicable for minimally invasive surgical techniques. More particularly, the present invention relates to an improved movable cutting cannula of sufficient size to allow the passage therethrough of tissue specimens or surgical instruments wherein one cannula is movable relative to another cannula to cut tissue.

Removal of tissue from a patient's body for disposal or analysis is commonly required in surgical procedures. Typically, cutting instruments have been used to separate small portions of tissue from the patient's body, and grasping or suction devices have been used to retrieve the tissue. For removal of small organs or tissue in laparoscopic or endoscopic surgical procedures, combination instruments that combine cutting and suction functions are known. Such dual function cutting/suction instruments can include a cutting instrument disposed inside a tube having a notch or other opening to permit the cutting instrument to have selective access to body tissue.

A single assembly that allows the irrigation, cutting, and suction functions to be carried out single-handedly by a surgeon would be highly desirable, and the cutter of the present invention may be incorporated into such a multi-function device. The cutter of the present invention may be used on any type of cannula-type device.

Notched cannulas having internally driven cutting tubes to cut tissue are known. For example, U.S. Pat. No. 4,099,529 to Peyman; U.S. Pat. Nos. 4,111,207 and 4,011,869 to Seiler, Jr.; U.S. Pat. No. 4,589,414 to Yoshida et al.; and U.S. Pat. No. 5,355,671 and U.S. Pat. application Ser. Nos. 07/830,580 and 08/060,423 to Clement and assigned to Mectra Labs, Inc. all describe surgical cutting instruments terminating in a cannula having a notch.

The present invention provides a surgical assembly for removal of body tissue. Preferably, the entire assembly is used a single time, and is constructed from low-cost, disposable materials. A preferred embodiment of the surgical assembly includes an outer cannula having an open distal end, a proximal end, and a side wall defining an interior region. During a surgical operation, the distal end of the cannula is inserted into a patient's body. A first notch is defined at the distal end of the cannula to permit access to the interior region. In practice, tissue is maneuvered into the notch prior to removal of the tissue from the body.

An annular blade is fixed to the distal end of the outer cannula and is arranged so that an annular gap is formed between the annular blade and the outer cannula. The annular blade has a proximal edge formed to include a cutting edge for cutting tissue received in the notch and the cutting edge is positioned to lie adjacent to the notch.

A hollow inner cannula is movably positioned in the interior region of the outer cannula. The inner cannula defines a cannula passageway, and a cutting edge for cutting tissue is provided on the inner cannula. The cutting edge is positioned to cut tissue that has entered the interior region of the outer cannula through the first notch. The cutting edge is additionally positioned to be received by the gap when the cutting edge is in the cutting position.

Means for removing the cut tissue from the inner cannula such as a vacuum source may be coupled to the inner cannula. This vacuum draws cut tissue out of the assembly and stores it in a storage chamber for later analysis. Means for supplying a saline solution for flow into the patient's body may also be coupled to the inner cannula if an irrigation feature is desired.

In summary, an improved cutting mechanism is provided by the use of an exterior and an interior concentric cannula that are arranged to form a gap adjacent to the notch in the exterior cannula. A hollow intermediate cannula having a cutting edge is arranged so that the cutting edge can be received within the gap. When tissue to be dissected is extended through the notch and across the gap, the passing of the intermediate cannula across the notch to the gap is effective for severing the tissue. The addition of the interior cannula provides a significant improvement in the effectiveness of the cutting tool.

According to the present invention, a surgical cutter for removal of body tissue during surgery is provided. The cutter includes a cannula having a proximal end and a distal end and a side wall defining an interior region. The distal end is positionable into a patient's body during surgery while the proximal end remains outside of the patient's body. The side wall is formed to include an orifice having a proximal edge and a distal edge and the orifice is arranged for receiving body tissue. Additionally, means for providing suction to the interior region may be included with the cutter.

A first annular wall is fixed to the distal end of the cannula. The first annular wall has a proximal edge. The wall is arranged to define an annular gap between the first annular wall and the side wall of the cannula.

An annular intermediate wall is also provided. The annular intermediate wall has an annular distal edge sized to be received by the gap. The annular intermediate wall and the cannula are arranged for relative axial movement between a first position with the intermediate wall remote from the orifice and a second position with the intermediate wall received in the gap to cut tissue received in the orifice.

In one version, the first annular wall is disposed within the interior region of the cannula. As a result, the gap and hence the annular intermediate wall are also positioned to lie within the interior region. In this version, the cannula is fixed to the cutter and the intermediate wall reciprocates inside of the cannula between the first position and the second position, though it will be apparent to one skilled in the art that the intermediate wall can be fixed and the cannula and first annular wall can reciprocate to achieve the same result. In a first embodiment the edges of the orifice are not cutting edges, however in a second embodiment, cutting edges are provided on the edges of the orifice.

In another embodiment, the first annular wall is disposed outside of the interior region of the cannula. As a result, the gap and hence the annular intermediate wall are also positioned to lie outside of the interior region. In this embodiment, the cannula is fixed to the cutter and the intermediate wall reciprocates outside of the cannula between the first position and the second position. Again, it will be apparent to one skilled in the art that the intermediate wall can be fixed and the cannula and first annular wall can reciprocate to achieve the same result.

Some preferred embodiments of this invention include a cannula with a distal end formed to include an aperture in fluid communication with the interior region. This aperture facilitates the introduction of carbon dioxide gas or saline solution into the patient's body, both of which are useful to the procedures for which the instrument is necessary. However, it will be apparent to one skilled in the art that whether the distal end of the cannula is open including an aperture or is closed with no aperture has no bearing on the performance of the tissue cutter of the present invention.

It has been found that to achieve the best tissue removal results, the cutting edges of the tissue cutter of the present invention can be formed using electrical discharge machining (EDM) and an electrical etching technique. EDM forms a surgically sharp edge on the cutting edge and is followed by the electrical etching process. The electrical etching process involves exposing the edge to a solution including phosphoric acid and sulfuric acid while the edge is at an electrical potential of approximately twelve volts D.C. The etching process alters the shape of the cutting edge resulting in a more effective instrument.

Other objects and advantages of the invention will become apparent from the following description of a preferred embodiment presently perceived as the best mode for practice of the invention and consideration of the accompanying drawings.

DETAILED DESCRIPTION OF THE DRAWINGS

Figure 1:
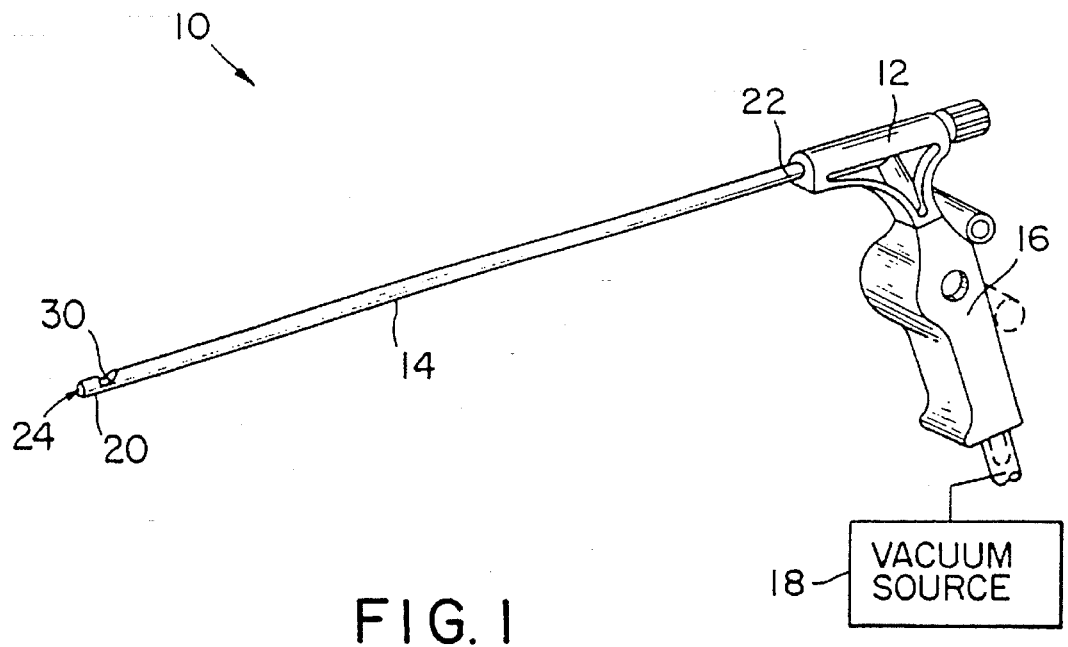
FIG. 1 is a perspective view of a tissue removal assembly including a cannula having a notch defined in its distal end and a conduit piece appended to a hand held valve providing a pistol-type grip illustratively connected to a vacuum source.

As illustrated in FIG. 1, a tissue removal assembly 10 useful for laparoscopic, endoscopic, or other surgical procedures includes a conduit piece 12 interconnecting a cannula 14 and a hand held valve 16. Suitable hand held valves are described in U.S. Pat. No. 5,019,054, to Clement et al., issued May 28, 1991, and assigned to Mectra Labs, Inc., the disclosure of which is incorporated herein by reference. Typically, a surgeon supports the assembly 10 with one hand holding the hand held valve 16, leaving the other hand free for manipulation of other instruments.

The tissue removal assembly 10 is useful for removing small organs, scar tissue, growths, biopsy samples, or other tissue from a patient's body. The tissue removal assembly 10 can also be used to cut away tissue for later analysis or disposal.

The tissue removal assembly 10 in FIG. 1 is illustratively connected to a vacuum source 18 to facilitate the removal of dissected tissue or other byproducts of procedures performed using the tissue removal assembly 10. The tissue removal assembly 10 can also be connected to a source of fluids such as a saline solution for introduction of these fluids into a patient's body.

In preferred embodiments, the tissue removal assembly 10 is disposed of after a single use, minimizing problems related to sterilization, storage, and maintenance of reusable instruments. Construction from low cost, easily incinerated or disposed of materials, which may include molded plastics, is contemplated.

As shown in FIG. 1, the cannula 14 extends longitudinally in a straight line, although curved, bent, flexible, or other conventional cannula designs are also contemplated. The cannula 14 has a distal end 20 for insertion into a patient's body and a proximal end 22 connected to the conduit piece 12. The distal end 20 of the cannula 14 terminates in a tip opening or aperture 24 that allows ingress or egress of solids, liquids, or gasses from a cannula interior region 26 defined by the cannula 14 and illustrated in FIGS. 2–7. The cannula interior region 26 is defined between the respective distal and proximal ends 20 and 22 of the cannula 14 to accept and allow bi-directional passage therethrough of solids, liquids, or gasses. Fluids, instruments, or gasses can be introduced from the proximal end 22 for effective operation in a patient's body at the distal end 20, or fluid (blood, etc.), solids (such as tissue samples), or gasses (such as may be produced by laser ablation and vaporization) at the operating site can be withdrawn from the distal end 20 through the cannula interior region 26.

The cannula 14 is dimensioned to conformably fit into the conduit piece 12, and is rigidly held in position by adhesives, welding, friction tight fit, or other suitable attachment mechanism to the conduit piece 12. Since the proximal end 22 of the cannula 14 is held within the conduit piece 12, fluid communication (as well as passage of medical instruments or tissue samples) is maintained between the conduit piece 12, the valve 16, the cannula interior region 26, and the aperture 24.

The distal end 20 of the cannula 14 is configured to assist in the capture and retention of body tissue 28 at an operating site in a patient's body, as best shown in FIGS. 2–7. A notch 30 having a proximal end 48 and a distal end 50 is defined in the distal end 20 of the cannula 14, immediately adjacent to the aperture 24 of the cannula 14. Like the aperture 24, the notch 30 allows access to the cannula interior region 26.

Figure 2:
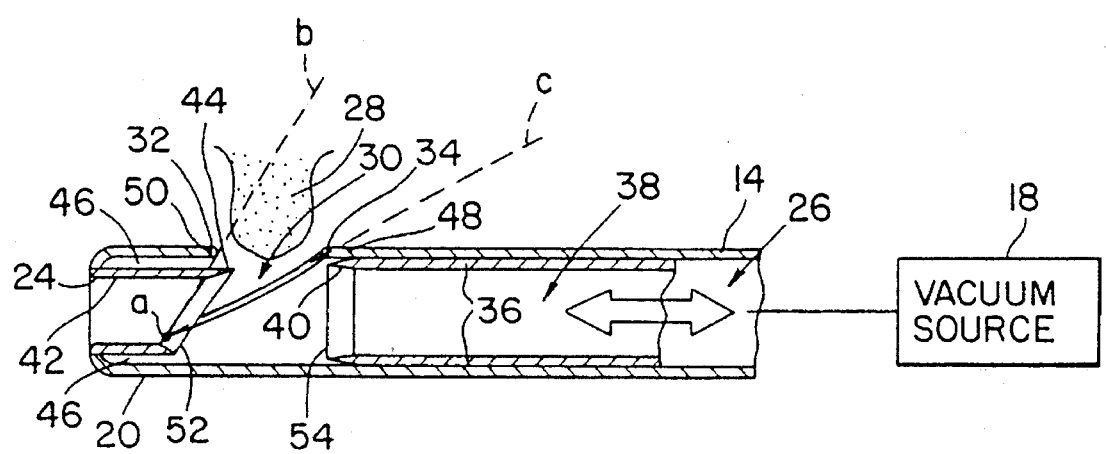
FIG. 2 is a sectional side view of the distal end of the cannula illustrated in FIG. 1, showing the position of the fixed annular blade adjacent to the notch and the intermediate cutter in a first position adjacent to the proximal end of the notch before tissue is maneuvered into the cannula interior through the notch.
Figure 3:
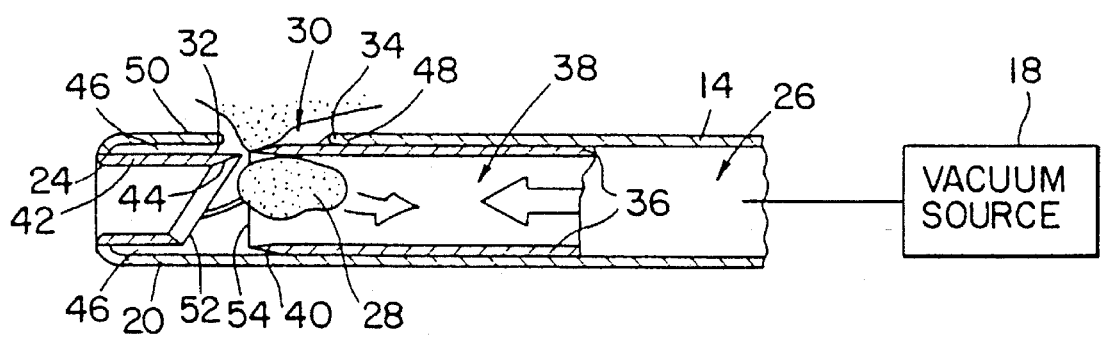
FIG. 3 is a view similar to FIG. 2, showing the position of tissue caught and maneuvered into the cannula interior through the notch and the intermediate cutter in a second position adjacent to the distal end of the notch to dissect tissue for removal for analysis or disposal.

In a first embodiment illustrated in FIGS. 2 and 3, the notch 30 is cut in the cannula 14 to define a first catch 32 and an oppositely directed second catch 34. As illustrated in FIG. 2, the notch 30 is formed by removal of a portion of the distal end 20 of the cannula 14. Two cuts into cannula 14 are made along planes indicated by lines b and c (planes b and c both extend perpendicular to the page in the illustration). The cuts along planes b and c terminate at a line of intersection between planes b and c (the line extends perpendicular to the page and is represented by a point a).

Figure 4:
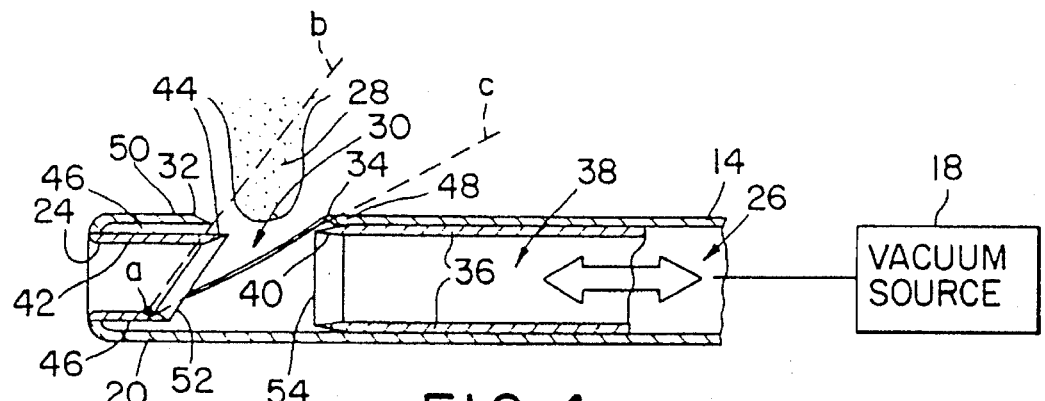
FIG. 4 is a sectional side view of the distal end of the cannula illustrated in FIG. 1, showing the notch having cutting edges and showing the position of the fixed annular blade adjacent to the notch and the intermediate cutter in a first position adjacent to the proximal end of the notch before tissue is maneuvered into the cannula interior through the notch.
Figure 5:
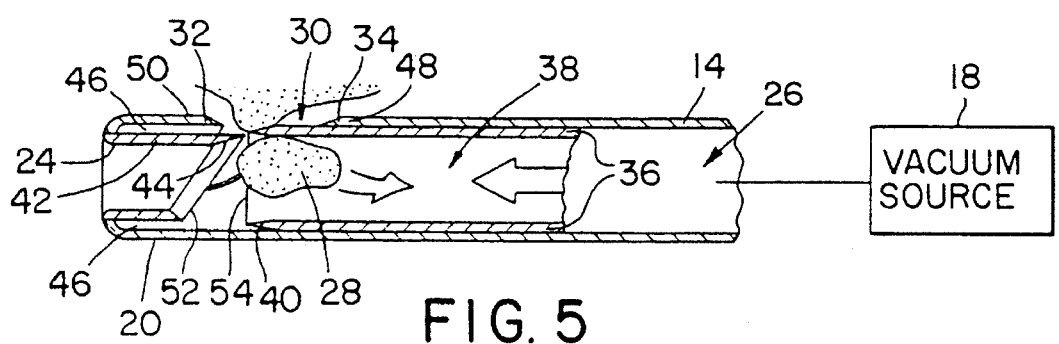
FIG. 5 is a view similar to FIG. 4, showing the position of tissue caught and maneuvered into the cannula interior through the notch and the intermediate cutter in a second position adjacent to the distal end of the notch to dissect tissue for removal for analysis or disposal.

In a second embodiment illustrated in FIGS. 4 and 5, the notch 30 is formed in a similar manner to the notch 30 of the first embodiment by cuts along planes b and c that terminate at a line of intersection between planes b and c (the line extends perpendicular to the page and is represented by a point a). After the notch 30 is formed, the edges 48, 50 of the notch 30 are formed into cutting edges as described below.

Figure 6:
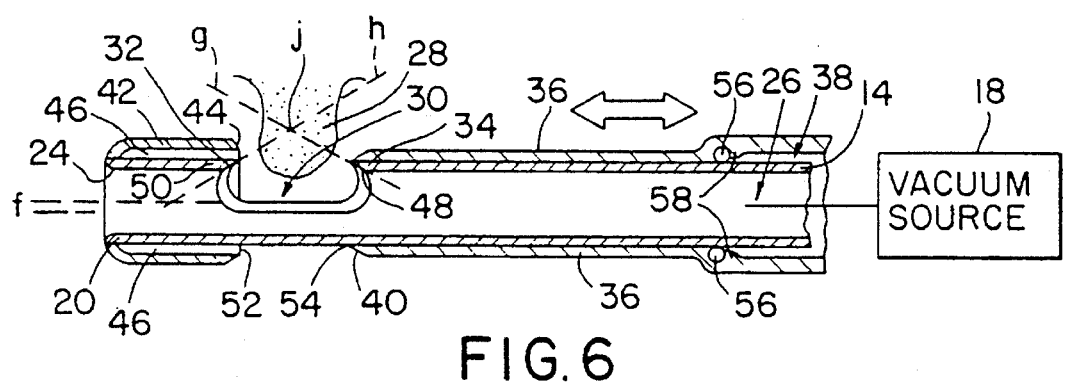
FIG. 6 is a cross sectional side view of the distal end of the cannula illustrated in FIG. 1, showing an embodiment of a tissue cutter including a pair of oppositely directed catches located on either side of the notch to assist in capture of tissue, a fixed annular blade adjacent to the notch, and an intermediate cutter movably positioned outside of the interior region of the cannula in a first position adjacent to the proximal end of the notch.
Figure 7:
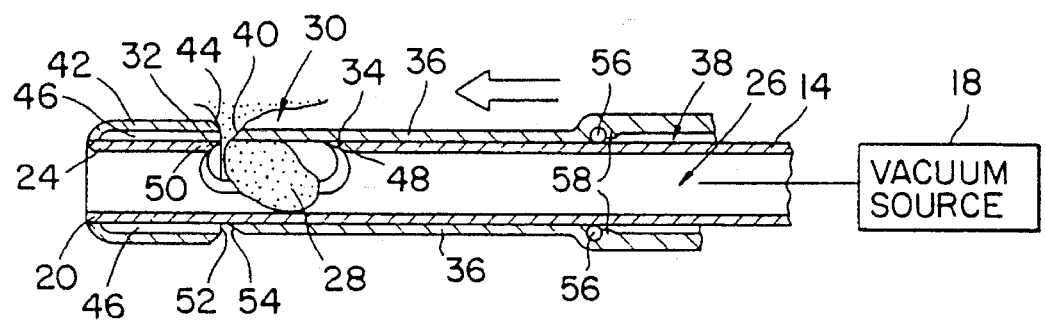
FIG. 7 is a view similar to FIG. 6, showing the position of tissue caught and maneuvered into the cannula interior through the notch and the intermediate cutter in a second position adjacent to the distal end of the notch to dissect tissue for removal for analysis or disposal.

In a third embodiment illustrated in FIGS. 6 and 7, the notch 30 is cut in the cannula 14 to define a first catch 32 and an oppositely directed second catch 34. As illustrated in FIG. 6, the notch 30 is formed by removal of a portion of the distal end 20 of the cannula 14. Two cuts into cannula 14 are made along oppositely directed planes indicated by lines g and h (planes g and h both extend perpendicular to the page in the illustration). The cuts along planes g and h terminate at their respective intersection with a longitudinally directed plane indicated by line f (plane f also extends perpendicular to the page). When a line of intersection between planes g and h is defined outside the cannula 14 (the line extends perpendicular to the page and is represented by a point j), a dihedral angle gh between planes g and h is defined. Typically, the dihedral angle gh is between about 30 degrees and 150 degrees, and is illustrated in FIG. 6 as about 120 degrees.

In practice, the notch 30 and catches 32 and 34 can be easily formed by two cuts into the cannula 14 along planes b and c or by three cuts into the cannula 14 along planes f, g, and h. More complex cutting, forming, molding, or castings can also be used to provide catches of differing shape. In addition, instead of forming catches from the body of the cannula, it is also contemplated to provide oppositely directed catches attached or affixed to a cannula adjacent to a notch. Multiple catches or several notches may also be used to enhance tissue grabbing or retention effectiveness.

In a first embodiment and a second embodiment illustrated in FIGS. 2, 3 and 4, 5, an annular blade 42 having a substantially tubular configuration is disposed within the distal end 20 of the cannula 14. The annular blade 42 and the cannula 14 are arranged to form a concentric annular gap 46 therebetween. The proximally directed end 52 of the annular blade 42 has a sharpened edge 44. To enhance cutting efficiency, the sharpened edge 44 is created by a traverse, slanting, and non-perpendicular cut across the annular blade 42. The resultant elliptically shaped cylinder edge is sharpened to give a beveled edge, with the bevel being directed inward toward the cannula interior region 26. Of course, perpendicular cuts across an annular blade 42 to give a circular edge, or other cutter edge configurations apparent to those skilled in the art may be substituted for the illustrated annular blade 42 embodiment.

In a third embodiment illustrated in FIGS. 6 and 7, an annular blade 42 having a substantially tubular configuration is disposed outside of the distal end 20 of the cannula 14. The annular blade 42 and the cannula 14 are arranged to form a concentric annular gap 46 therebetween. The proximally directed end 52 of the annular blade 42 has a sharpened edge 44. The sharpened edge 44 is created by a perpendicular cut across the annular blade 42. The resultant circular shaped cylinder edge is sharpened to give a beveled edge, with the bevel being directed inward toward the cannula interior region 26. Of course, traverse, slanting, and non-perpendicular cuts across an annular blade 42 to give a elliptical edge, or other cutter edge configurations apparent to those skilled in the art may be substituted for the illustrated annular blade 42 embodiment.

In operation, as illustrated in FIGS. 2, 4, and 6, catches 32 and 34 enhance tissue grabbing and holding effectiveness, allowing a surgeon to maneuver the distal end 20 to catch and hold a piece of body tissue 28. After body tissue 28 has been positioned in the notch 30, an intermediate cutter 36 can be moved forward from its first position in the cannula interior region 26 to a second position toward the distal end 20 of the cannula 14 to cut and/or assist in retaining tissue in the notch 30, as shown in FIGS. 3, 5, and 7.

As illustrated in FIGS. 2–7, the intermediate cutter 36 is an annular wall having a substantially tubular configuration, defining a cutter interior region 38 therethrough. In addition, the distally directed end 54 of the intermediate cutter 36 has a sharpened edge 40 that is positioned to be received in the gap 46 when the intermediate cutter 36 is in its second position. The sharpened edge 40 is created by a perpendicular cut across the intermediate cutter 36. The resultant circularly shaped cylinder edge is sharpened to give a beveled edge, with the bevel being directed inward toward the cannula interior region 26. Of course, traverse, slanting, and non-perpendicular cuts across a cutter to give an elliptical edge, or other cutter edge configurations apparent to those skilled in the art may be substituted for the illustrated cutter embodiment.

The cutting edges 40, 44, and cutting edges 48, 50 of the second and third embodiments of the tissue cutter of the present invention are formed using an electrical etching technique. This technique includes the steps of electrical discharge machining the edge 40, 44, 48, 50 to surgical sharpness and electrically etching the edge 40, 44, 48, 50. The electrical etching process involves exposing the edge 40, 44, 48, 50 to a solution including phosphoric acid and sulfuric acid while the edge 40, 44, 48, 50 is at an electrical potential of approximately twelve volts D.C. The etching process alters the shape of the cutting edge 40, 44, 48, 50 resulting in a more effective instrument.

In the first and second embodiments illustrated in FIGS. 2–5, the intermediate cutter 36 is sized to snugly fit into the cannula interior region 26, with its outer diameter being slightly less than the inner diameter of the cannula 14. When tissue has been engaged by catches 32 and 34 and maneuvered into the cannula interior region 26 through the notch 30, the intermediate cutter 36 is moved forward from its normal position on the proximal side of the notch 30 in the cannula interior region 26 illustrated in FIGS. 2 and 4 to a cutting position in the region of the notch 30 illustrated in FIGS. 3 and 5. When the intermediate cutter 36 passes through the cannula interior region 26 to cover the region of the notch 30 any tissue entrapped in the cannula interior region 26 is severed by the sharpened edges 40, 44. This severed, dissected tissue can be drawn by surgical instruments, or preferably by suction pressure, through the cutter interior region 38, toward the proximal end 20 of the cannula interior region 26, into the conduit piece 12 and to a storage or disposal site.

In a third embodiment illustrated in FIGS. 6 and 7, the intermediate cutter 36 is sized to snugly fit around the cannula 14, with its inner diameter being slightly greater than the outer diameter of the cannula 14. A resilient o-ring 56 sealingly engages the cannula 14 and the intermediate cutter 36 and is held into position by an annular stop 58 appended to the intermediate cutter 36. When tissue has been engaged by catches 32 and 34 and maneuvered into the cannula interior region 26 through the notch 30, the intermediate cutter 36 is moved forward from its normal position on the proximal side of the notch 30 illustrated in FIG. 6, to a cutting position in the region of the notch 30 illustrated in FIG. 7. When the intermediate cutter 36 passes over the cannula 14 to cover the region of the notch 30 any tissue entrapped in the cannula interior region 26 is severed by the sharpened edges 40, 44. As with the first embodiment, this severed, dissected tissue can be drawn by surgical instruments, or preferably by suction pressure, through the cutter interior region 38, toward the proximal end 22 of the cannula interior region 26, into the conduit piece 12 and to a storage or disposal site.

Dissected tissue or fumes from vaporized tissue may be removed from the cannula by suction produced by fluid connection a vacuum source 18. The vacuum source 18 can be replaced by a source of fluids such as a saline solution for introduction of these fluids into the patient's body. The operation of the rotary valve 16 for disposing or retaining tissue samples or waste byproducts of the procedures performed using a lavage with a tissue cutter of the present invention is described in great detail in patent application Ser. No. 08/060,423 to Clement, filed May 11, 1993 and assigned to Mectra Labs, Inc., the disclosure of which is hereby incorporated by reference.

Although the invention has been described in detail with reference to a preferred embodiment, variations and modifications exist within the scope and spirit of the invention as described and defined in the following claims.

I claim:

1. A surgical cutter for removal of body tissue during surgery, the surgical cutter comprising
   a cannula having a proximal end and a distal end and a side wall defining an interior region, the distal end being positionable into a patient's body during such surgery with the proximal end outside of the body, the side wall being formed to include an orifice for receiving body tissue, the orifice having a distal edge,
   means for providing suction in the interior region,
   a first annular wall fixed to the distal end of the cannula and having a proximal edge, the first annular wall arranged to define an annular gap disposed between the first annular wall and the cannula side wall, and
   an annular intermediate wall having an annular distal edge sized to be received by the gap, the annular intermediate wall and the cannula being arranged for relative axial movement between a first position with the intermediate wall remote from the orifice and a second position with the intermediate wall received in the gap to cut tissue received in the orifice.

2. The surgical cutter of claim 1, wherein the first annular wall is disposed within the interior region.

3. The surgical cutter of claim 2, including means for reciprocating the annular intermediate wall between the first position and the second position.

4. The surgical cutter of claim 2, wherein the proximal edge of the first annular wall extends farther in a proximal direction than the distal edge of the orifice.

5. The surgical cutter of claim 1, wherein the distal end of the cannula is formed to include an aperture in fluid communication with the interior region.

6. The surgical cutter of claim 5 including means for providing a liquid solution to the interior region for flow of the solution into the patient's body.

7. The surgical cutter of claim 1, wherein the first annular wall is disposed outside of the side wall of the cannula.

8. The surgical cutter of claim 7, including means for reciprocating the annular intermediate wall between the first position and the second position.

9. The surgical cutter of claim 8, wherein an O-ring sealingly engages the cannula and the annular intermediate wall sealingly engages the O-ring.

10. The surgical cutter of claim 1, wherein the proximal edge of the first annular wall adjacent the orifice extends axially a distance further from the distal end of the cannula than the distal edge of the orifice.

11. The surgical cutter of claim 10, wherein the proximal edge of the first annular wall is arranged to angle away from the orifice toward the distal end of the cannula.

12. The surgical cutter of claim 1, wherein the distal edge of the intermediate annular wall includes a cutting edge.

13. The surgical cutter of claim 12, wherein the cutting edge is prepared by sharpening and electrically etching the distal edge of the intermediate annular wall.

14. The surgical cutter of claim 1, wherein the distal edge of the orifice includes a cutting edge.

15. The surgical cutter of claim 14, wherein the cutting edge is prepared by sharpening and electrically etching the distal edge of the orifice.

16. The surgical cutter of claim 1, wherein the proximal edge of the first annular wall includes a cutting edge.

17. The surgical cutter of claim 16, wherein the cutting edge is prepared by sharpening and electrically etching the proximal edge of the inner wall.

18. A surgical cutter for removal of body tissue during surgery, the surgical cutter comprising
   an outer cannula having a proximal end, a distal end being positionable into a patient's body during such surgery with the proximal end outside of the body, and a side wall defining an interior region, the interior region defining a cavity in fluid communication with a vacuum source, the side wall being formed to include an orifice arranged to receive body tissue, the orifice having a proximal edge and a distal edge,
   an inner cannula having a distal end formed to include a cutting edge and a side wall defining a second interior region, the inner cannula being disposed in the interior region of the outer cannula, the inner cannula and the outer cannula being slidably coupled for relative axial movement between a first position with the cutting edge remote from the orifice and a second position with the cutting edge adjacent the distal edge of the orifice, the inner cannula and the outer cannula being movable between the first position and the second position so that the cutting edge passes the orifice, and
   an annular blade including a proximal edge disposed at the distal end of the outer cannula adjacent the orifice, the proximal edge of the annular blade arranged to oppose the cutting edge, the annular blade being arranged so that the annular blade is positioned inside of the second interior region when the inner cannula is in the second position.

19. The surgical cutter of claim 18, wherein the outer cannula is fixed to the surgical cutter and the inner cannula reciprocates between the first position and the second position.

20. The surgical cutter of claim 18, wherein the proximal edge of the annular blade adjacent the orifice extends axially a distance further from the distal end of the outer cannula than the distal edge of the orifice.

21. The surgical cutter of claim 20, wherein the proximal edge of the annular blade is arranged to angle away from the orifice toward the distal end of the outer cannula.

22. The surgical cutter of claim 18, wherein the distal end of the outer cannula is formed to include an aperture in fluid communication with the cavity.

23. The surgical cutter of claim 22, wherein the cavity is in fluid communication with a liquid or gaseous solution source for flow of the solution into the patient's body.

24. The surgical cutter of claim 18, wherein the cutting edge is prepared by sharpening and electrically etching the distal end of the inner cannula.

25. The surgical cutter of claim 18, wherein the proximal edge of the annular blade includes a second cutting edge.

26. The surgical cutter of claim 25, wherein the second cutting edge is prepared by sharpening and electrically etching the proximal edge of the annular blade.

27. The surgical cutter of claim 18, wherein the distal edge of the orifice includes a third cutting edge.

28. The surgical cutter of claim 27, wherein the third cutting edge is prepared by sharpening and electrically etching the distal edge of the orifice.

29. A surgical cutter for removal of body tissue during surgery, the surgical cutter comprising an inner cannula having a proximal end, a distal end being positionable into a patient's body during such surgery with the proximal end outside of the body, and a side wall defining an interior region, the interior region defining a cavity in fluid communication with a vacuum source, the side wall being formed to include an orifice arranged to receive body tissue, the orifice having a proximal edge and a distal edge, an outer cannula having a distal end formed to include a cutting edge and a side wall defining a second interior region, the inner cannula being disposed in the second interior region of the outer cannula, the inner cannula and the outer cannula being slidably coupled for relative axial movement between a first position with the cutting edge remote from the orifice and a second position with the cutting edge adjacent the distal edge of the orifice, the inner cannula and the outer cannula being movable between the first position and the second position so that the cutting edge passes the orifice, and an annular blade including a proximal edge disposed at the distal end of the inner cannula adjacent the orifice, the annular blade arranged to oppose the cutting edge, the annular blade being arranged so that the annular blade is positioned outside of the outer cannula when the outer cannula is in the second position.

30. The surgical cutter of claim 29, wherein the inner cannula is fixed to the surgical cutter and the outer cannula reciprocates between the first position and the second position.

31. The surgical cutter of claim 29, wherein an O-ring sealingly engages the inner cannula and the outer cannula sealingly engages the O-ring.

32. The surgical cutter of claim 29, wherein the distal end of the inner cannula is formed to include an aperture in fluid communication with the cavity.

33. The surgical cutter of claim 32, wherein the cavity is in fluid communication with a liquid or gaseous solution source for flow of the solution into the patient's body.

34. The surgical cutter of claim 29, wherein the cutting edge is prepared by sharpening and electrically etching the distal end of the outer cannula.

35. The surgical cutter of claim 29, wherein the proximal edge of the annular blade includes a second cutting edge.

36. The surgical cutter of claim 35, wherein the second cutting edge is prepared by sharpening and electrically etching the proximal edge of the annular blade.

37. The surgical cutter of claim 29, wherein the distal edge of the orifice includes a third cutting edge.

38. The surgical cutter of claim 37, wherein the third cutting edge is prepared by sharpening and electrically etching the distal edge of the orifice.

39. A tissue cutter for use during surgery comprising a pair of concentrically arranged cannula forming a concentric gap between the innermost and the outermost cannula, the innermost cannula providing a first cutting edge opening into the gap, and a third cannula movable relative to the pair of cannula into the gap, the third cannula having a second cutting edge to cooperate with the first cutting edge.

40. The tissue cutter of claim 39, wherein the second cutting edge is prepared by sharpening and electrically etching the third cannula.

41. The tissue cutter of claim 39, wherein the first cutting edge is prepared by sharpening and electrically etching the innermost cannula.

42. The tissue cutter of claim 39, wherein the outermost cannula is formed to include an orifice sized to accept body tissue and the orifice includes a proximal edge and a distal edge and the distal edge is positioned to lie adjacent to the first cutting edge.

43. The tissue cutter of claim 42, wherein the distal edge of the orifice includes a third cutting edge.

44. The tissue cutter of claim 43, wherein the third cutting edge is prepared by sharpening and electrically etching the distal edge of the orifice.

45. The tissue cutter of claim 39, wherein the outermost cannula includes a side wall arranged to define an interior region that is in fluid communication with a source chamber.

46. The tissue cutter of claim 45, wherein the source chamber is a vacuum source for providing suction to the interior region.

47. The tissue cutter of claim 45, wherein the source chamber is a liquid solution source arranged to provide solution to the interior region for flow of the solution into the patient's body.

48. The tissue cutter of claim 45, wherein the innermost cannula is formed to include an aperture adjacent to the side wall and in fluid communication with the interior region.

49. The tissue cutter of claim 39, wherein the innermost cannula is fixed to the tissue cutter.

50. The tissue cutter of claim 39, wherein the pair of concentrically arranged cannula are fixed to the tissue cutter.

* * * * *